United States Patent [19]

Rauleder et al.

[11] 4,212,809

[45] Jul. 15, 1980

[54] PROCESS FOR THE PREPARATION OF 5-(OXIRANYLMETHYL)-1,3-BENZODIOXOLE

[75] Inventors: Gebhard Rauleder, Duesseldorf; Helmut Waldmann, Leverkusen; Volker Mues, Wuppertal; Hermann Seifert, Cologne, all of Fed. Rep. of Germany

[73] Assignee: Bayer Aktiengesellschaft, Leverkusen, Fed. Rep. of Germany

[21] Appl. No.: 967,448

[22] Filed: Dec. 7, 1978

[30] Foreign Application Priority Data

Dec. 24, 1977 [DE] Fed. Rep. of Germany ....... 2757926

[51] Int. Cl.² .......................................... C07D 317/44
[52] U.S. Cl. .............................................. 260/340.5 R
[58] Field of Search ..................... 260/340.5 R, 348.25

[56] References Cited

U.S. PATENT DOCUMENTS 3,954,815  5/1976  Fisher ........................... 260/348.5 L

FOREIGN PATENT DOCUMENTS 2630107  1/1977  Fed. Rep. of Germany  260/340.5 R X

OTHER PUBLICATIONS

Payne, Tetrahedron 18, 763 (1962).
Boeseken et al., Rec. Trav. Chim. 48, 363–369 (1929).
Autennis et al., Org. Magn. Resonance, 1972, vol. 4, p. 486.

Primary Examiner—Ethel G. Love
Attorney, Agent, or Firm—Sprung, Felfe, Horn, Lynch & Kramer

[57] ABSTRACT

The invention relates to a process for the provision of 5-(oxiranylmethyl)-1,3-benzodioxole by reaction of 5-(2-propenyl)1,3-benzodioxole with a percarboxylic acid having 1 to 8 carbon atoms in an inert organic solvent.

13 Claims, No Drawings

PROCESS FOR THE PREPARATION OF 5-(OXIRANYLMETHYL)-1,3-BENZODIOXOLE

The present invention relates to a process for the preparation of 5-(oxiranylmethyl)-1,3-benzodioxole from 5-(2-propenyl)-1,4-benzodioxole and percarboxylic acids.

5-(Oxiranylmethyl)-1,3-benzodioxole can be used in the field of plant protection (cf. M. C. Bowman and M. Beroza, Residue Reviews 17, 1–22 (1967)), as a monomer for the production of polymers, e.g. epoxy resins, and as an organic intermediate product, e.g. so as to prepare, by means of the addition of water to 5-(oxiranylmethyl)-1,3-benzodioxole, the corresponding diol which can be further reacted to form polyethers.

The reaction of piperonal with diazomethane in a mixture of ether and methanol as the solvent at −15° C. was published by Mosettig in 1929. 5-(Oxiranylmethyl)-1,3-benzodioxole is said to be formed as the main product in this reaction. (E. Mosettig, Ber. d. Dtsch. Chem. Ges. 62, page 1,271 (1929)).

In order to identify the reaction product, 5-(oxiranylmethyl)-1,3-benzodioxole was also prepared by another synthesis path. In particular, 5-(2-propenyl)-1,3-benzodioxole was treated with iodine and mercury-II oxide and this reaction mixture was then shaken with powdered potassium hydroxide. However, because of the toxicity and danger of the reactants used, neither of the two methods is suitable for the industrial preparation of 5-(oxiranylmethyl)-1,3-benzodioxole.

The preparation of 5-(oxiranylmethyl)-1,3-benzodioxole from the bromohydrin of 5-(2-propenyl)-1,3-benzodioxole by treatment with a base, as described by Barnes in 1974 (R. A. Barnes, Int. Congr. Essent. Oils, 6th, 1974, page 132), is likewise unsuitable for an industrial preparation since bromine is too expensive a starting material and waste salts which pollute the environment are obtained during the reaction.

Furthermore, attempts have been made to carry out the epoxidation of 5-(2-propenyl)-1,3-benzodioxole in accordance with the method of Payne (G. Payne, Tetrahedron 18, 763 (1962)) using hydrogen peroxide in the presence of benzonitrile. However, the yield of 5-(oxiranylmethyl)-1,3-benzodioxole achieved was only 5% (M. Antennis, F. Borremans, Von den Bossche and G. Verhegge, Org. Magn. Resonance, 1972, volume 4, page 486).

In 1929, Böeseken and Elsen reported the attempt to apply the Prileschajew reaction (N. Prileschajew, Ber. dtsch. chem. Ges. 42, 4,811 (1909)) for the preparation of 5-(oxiranylmethyl)-1,3-benzodioxole (J. Böeseken and G. Elsen, Rec. drav. chim. 48, 363-9 (1929)). They reacted 5-(2-propenyl)-1,3-benzodioxole with peracetic acid. Although they carried out the reaction at low temperature, they obtained as the reaction product only the acetate resulting from the splitting of the oxirane ring in 5-(oxiranylmethyl)-1,3-benzodioxole with acetic acid.

Finally, 5-(oxiranylmethyl)-1,3-benzodioxole could be synthesised by using perbenzoic acid (M. Autennis, F. Borremans, Von den Bossche and G. Verhegge, Org.Magn. Resonance, 1972, volume 4, page 486). For the preparation of analytical amounts of 5-(oxiranylmethyl)-1,3-benzodioxole, 5-(2-propenyl)-1,3-benzodioxole was stirred with perbenzoic acid in chloroform as the solvent at 0° C. for 24 hours and the reaction solution was washed with 10% strength NaOH and distilled. 5-(Oxiranylmethyl)-1,3-benzodioxole was obtained in 60% yield. However, because of the unsatisfactory yield and the long reaction time, this preparation method is unsuitable for industrial application.

According to the publication by I. Varagnat, Ind. Eng. Chem. Prod. Res. Dev. volume 15, No. 3, page 212–213, (1976), percarboxylic acid reacts with phenol or pyrocatechol with hydroxylation of the nucleus. Since 5-(2-propenyl)-1,3-benzodioxole is a pyrocatechol derivative, this reaction must be reckoned with as a reaction competing with epoxidation in the attempt to react 5-(2-propenyl)-1,3-benzodioxole by the Prileschajew reaction, and leads to a decrease in the yield of 5-(oxiranyl-methyl)-1,3-benzodioxole.

In contrast, it has now been found, surprisingly, that 5-(oxiranylmethyl)-1,3-benzodioxole can be prepared in good yields and high purity when 5-(2-propenyl)-1,3-benzodioxole is reacted with a solution of a percarboxylic acid containing 1 to 8 carbon atoms in an inert organic solvent, using a molar ratio of 5-(2-propenyl)-1,3-benzodioxole to percarboxylic acid of 1.2 to 20/1 and at a temperature of −20° to +80° C.

Inert organic solvents which can be used are the most diverse hydrocarbons, for example, aliphatic hydrocarbons, such as hexane, heptane, octane, 2-ethylhexane, decane, dodecane, cyclohexane, methylcyclopentane and petroleum ether, and aromatic hydrocarbons, which can be optionally substituted, such as benzene, nitrobenzene, toluene, ethylbenzene, cumene, diisopropylbenzene, xylene and chlorobenzene, and oxygen-containing hydrocarbons, such as diethyl ether, diisopropyl ether, dibutyl ether, tetrahydrofurane, dioxane, acetone, methyl ethyl ketone, acetic acid ethyl ester, acetic acid methyl ester, acetic acid propyl ester, acetic acid butyl ester, propionic acid methyl ester, propionic acid ethyl ester, propionic acid propyl ester, butyric acid methyl ester, butyric acid ethyl ester, butyric acid propyl ester and butyric acid butyl ester, and chlorinated hydrocarbons, such as methylene chloride, chloroform, carbon tetrachloride, 1-chloroethane, 1,2-dichloroethane, 1,1-dichloroethane, 1,1,2,2-tetrachloroethane, 1-chloropropane, 2-chloropropane, 1,2-dichloropropane, 1,3-dichloropropane, 2,3-dichloropropane, 1,2,3-trichloropropane, 1,1,2,3-tetrachloropropane, butyl chloride, 1,2-dichlorobutane, 1,4-dichlorobutane, 2,3-dichlorobutane, 1,3-dichlorobutane, 1,2,3,4-tetrachlorobutane, tert.-butyl chloride, amyl chloride, 1,2-dichloropentane, 1,5-dichloropentane, 1,2,3,4-tetrachloropentane, cyclopentyl chloride, 1,2-dichlorocyclopentyl chloride, hexyl chloride, 1,2-dichlorohexane, 1,6-dichlorohexane, 1,2,3,4-tetrachlorohexane, 1,2,5,6-tetrachlorohexane, cyclohexyl chloride, 1,2-dichlorohexane, heptyl chloride, 1,2-dichloroheptane, 1,2,3,4-tetrachloroheptane, cycloheptyl chloride, 1,2-dichloroheptane, octyl chloride, 1,2-dichlorooctane, 1,2,3,4-tetrachlorooctane, cyclooctyl chloride and 1,2-dichlorooctane.

Preferred of the above solvents are methyl chloride, chloroform, carbon tetrachloride and 1,2-dichloropropane as chlorinated hydrocarbons; benzene, nitrobenzene, toluene and chlorobenzene as aromatic hydrocarbons; 2-ethyl-hexane, cyclohexane and methyl-cyclopentane as hydrocarbons; and acetone, tetrahydrofurane and propionic acid ethyl ester as oxygen-containing hydrocarbons.

Particularly preferred solvents are 1,2-dichloropropane and carbon tetrachloride of the chlorinated aliphatic carbons; benzene and chlorobenzene as aromatic hydrocarbons; cyclohexane as hydrocarbon and propionic acid ethyl ester as oxygen containing hydrocarbon.

Solvent mixtures of the various organic solvents indicated above can also be used.

Peracids, particularly only per mono- and di-carboxylic acids, with up to 8 C atoms which can be used according to the invention are peralkene carboxylic acids, such as per-alkane carboxylic acid with up to 5 carbon atoms, such as performic acid, peracetic acid, perpropionic acid, perbutyric acid, perisobutyric acid and pervaleric acid, are preferably suitable.

Perpropionic acid and perisobutyric acid are particularly preferably used. Perpropionic acid is very particularly preferred. The preparation of peracids, which are free from mineral acids, in one of the organic solvents mentioned can be carried out, for example, by the process described in DOS (German Published Specification) No. 2,262,970.

In general, the process according to the invention is carried out in practice in a temperature range from −20° to 80° C. It is preferably carried out at 0°–60° C. and particularly preferably at 30°–50° C. In special cases, the temperature can also be below or above the temperatures indicated.

Besides the procedure under isothermal conditions, that is to say maintaining a uniform temperature in the entire reaction mixture, it is also possible to carry out the reaction with a so-called temperature gradient being set up, which in general increases as the reaction progresses. However, the reaction can also be carried out in a manner such that a decrease in temperature gradient is set up as the reaction progresses.

According to the invention, the molar ratio of 5-(2-propenyl)-1,3-benzodioxole to percarboxylic acid is 1.2 to 20:1.0. A molar ratio of 2.0 to 15:1.0 can also be used. A molar ratio of 3.0 to 10:1.0 is preferably used. It is very particularly advantageous to use a molar ratio of 4 to 8 mols of 5-(2-propenyl)-1,3-benzodioxole per mol of peracid.

The process according to the invention can be carried out under the most diverse pressures. In general, it is carried out under normal pressure; however, the process can also be carried out under reduced pressure or excess pressure.

In general, the water content of the percarboxylic acid used for the epoxidation should be as low as possible. Low amounts of water of up to 5% by weight are in general not troublesome. A percarboxylic acid with a water content of up to 1% by weight, for example, is suitable. A percarboxylic acid solution which contains less than 0.5% by weight of water is preferably used. A water content of less than 0.1% by weight is particularly preferred.

The hydrogen peroxide content of the percarboxylic acid used can vary within wide limits, for example it can be 0.1 to 10% by weight. A percarboxylic acid with a hydrogen peroxide content of less than 2%, for example, is particularly suitable. However, it can also be advantageous to carry out the epoxidation with a percarboxylic acid which has a hydrogen peroxide content of less than 0.3%.

The mineral acid content of the percarboxylic acid solution used for the reaction should be as low as possible. It is advantageous to carry out the reaction with a percarboxylic acid solution which has a mineral acid content of less than 50 ppm. A mineral acid content of less than 10 ppm is particularly advantageous.

The reaction can be carried out discontinuously or continuously in the customary devices for reactions of this type, such as stirred kettles, boiling reactors, tube reactors, loop reactors or circulatory reactors.

Heavy metal ions in the reaction mixture catalyse the decomposition of the percarboxylic acid. Substances which inactivate the heavy metal ions by means of the formation of complexes are therefore generally added to the percarboxylic acid. Known substances of this type are gluconic acid, ethylenediaminetetraacetic acid, sodium silicate, sodium pyrophosphate, sodium hexametaphosphate, disodium dimethyl pyrophosphate or $Na_2(2\text{-ethylhexyl})_5(P_3O_{10})_2$ (DAS(German Published Specification) No. 1,056,596, column 4, line 60 et seq.).

5(2-Propenyl)-1,3-benzodioxole can be introduced in various ways into the device used for the reaction. It can be put into the reactor together with the percarboxylic acid solution, or the two components are fed into the ractor separately from one another. Furthermore, it is possible to introduce the olefin and the percarboxylic acid solution into the reactor unit at different points. If several reactors connected in a cascade are used, it can be appropriate to introduce all the olefin into the first reactor. However, it is also possible to distribute the olefin among the various reactors.

The heat of reaction is removed by internal or external coolers. In order to remove the heat of reaction it is also possible to carry out the reaction under reflux, that is to say in boiling reactors.

The reaction is appropriately carried out with as complete as possible a conversion of the percarboxylic acid. In general, more than 95 mol % of the percarboxylic acid are converted. It is appropriate to convert more than 98 mol % of the peracid.

The examples which follow illustrate the invention. Unless stated otherwise, all the percentage data represent percentages by weight.

EXAMPLE 1

19.90 g (0.11 mol) of 5-(2-propenyl)-1,3-benzodioxole were initially introduced into a double-walled flask having a stirrer and reflux condenser and are warmed to 40° C. 43.58 g (0.10 mol) of a 20.58% strength solution of perpropionic acid in benzene were added dropwise, whilst stirring, and stirring was continued at this temperature for a further 5 hours. Titrimetric analysis then showed a peracid conversion of 98%. Analysis of gas chromatography gave a selectivity for the 5-(oxiranylmethyl)-1,3-benzodioxole formed of 61%.

EXAMPLE 2

48.82 g (0.3 mol) of 5-(2-propenyl)-1,3-benzodioxole were reacted with 45 g (0.1 mol) of a 20% strength solution of perpropionic acid in dichloropropane at 30° C. as described in Example 1. After a reaction time of 6 hours, the peracid conversion was 96%. 5-(Oxiranylmethyl)-1,3-benzodioxole was formed with a selectivity of 68%.

EXAMPLE 3

20.38 g (0.125 mol) of 5-(2-propenyl)-1,3-benzodioxole were reacted with 10.55 g (0.0246 mol) of a 20.86% strength solution of perpropionic acid in benzene at 40° C. as described under Example 1. After 2 hours, the peracid conversion was 97%. The selectivity for the formation of 5-(oxiranylmethyl)-1,3-benzodioxole was 78%.

In order to remove the propionic acid, the reaction mixture was washed several times with water and distilled.

Yield: 3.07 g; purity: 99%.
Boiling point 0.5=96° C.

EXAMPLE 4

305 g of 5-(2-propenyl)-1,3-benzodioxole were reacted with 105 g of a 21.52% strength solution of perpropionic aicd in benzene at 32° C. as described in Example 1. After a reaction time of 2.5 hours, the peracid conversion was 98%. 5-(Oxiranylmethyl)-1,3-benzodioxole was formed with a selectivity of 85%. For working up, the reaction mixture was introduced into a distillation unit operating with a thin film evaporator and was separated into a top product, which contained benzene, propionic acid and unreacted 5-(2-propenyl)-1,3-benzodioxole, and into a bottom product, which consisted essentially of 5-(oxiranylmethyl)-1,3-benzodioxole. After redistillation of this bottom product, 37.0 g of 5-(oxiranylmethyl)-1,3-benzodioxole were obtained in a purity of 99.9%.

What is claimed is:

1. Process for the preparation of 5-(oxiranylmethyl)-1, 3-benzodioxole from 5-(2-propenyl)-1,3-benzodioxole and percarboxylic acids, which comprises reacting 5-(2-propylene)-1, 3-benzodioxole with a solution of a per-alkane carboxylic acid with up to 5 carbon atoms whereby the per-alkane carboxylic contains low amounts of water of up to 5% by weight, less than 2% by weight of hydrogen peroxide and less than 50 ppm of mineral acid, in an inert organic solvent, using a molar ratio of 5-(2-propenyl)-1,3-benzodioxole to percarboxylic acid of 1.2 to 20:1 and at a temperature of −20 to +80° C.

2. Process according to claim 1, wherein the reaction is carried out with a solution of a percarboxylic acid containing 1 to 5 carbon atoms.

3. Process according to claim 1 or 2, wherein peracetic acid is used as the percarboxylic acid.

4. Process according to claim 1 or 2, wherein perpropionic acid is used as the percarboxylic acid.

5. Process according to claim 1 or 2, wherein perisobutyric acid is used as the percarboxylic acid.

6. Process according to claim 1, wherein the reaction is carried out in a hydrocarbon as the organic solvent.

7. Process according to claim 1, wherein dichloropropane is used as the organic solvent.

8. Process according to claim 1, wherein propionic acid ethyl ester is used as the organic solvent.

9. Process according to claim 1, wherein benzene is used as the organic solvent.

10. Process according to claim 1, wherein the reaction is carried out using a molar ratio of 5-(2-propenyl)-1,3-benzodioxole to percarboxylic acid of 4 to 8:1.

11. Process according to claim 1, wherein the reaction is carried out at a temperature from 30° to 50° C.

12. Process according to claim 1, wherein the separation of the carboxylic acid, corresponding to the percarboxylic acid, formed during the reaction is carried out by extracting the reaction mixture with water.

13. Process according to claim 1, wherein the reaction mixture obtained after the reaction is introduced into a distillation unit and separated into a top product, which contains the solvent, the carboxylic acid corresponding to the percarboxylic acid and unreacted 5-(2-propenyl)-1,3-benzodioxole, and into a bottom product, which consists essentially of 5-(oxiranylmethyl)-1,3-benzodioxole.

* * * * *

UNITED STATES PATENT AND TRADEMARK OFFICE
CERTIFICATE OF CORRECTION

PATENT NO. :  4,212,809
DATED      :  July 15, 1980
INVENTOR(S) :  Gebhard Rauledar et al It is certified that error appears in the above-identified patent and that said Letters Patent are hereby corrected as shown below:

Column 3, line 7, "peralkene" should be --peralkane--.

Column 4, line 19, "ractor" should be --reactor--.

Column 5, line 5, should read :boiling point $_{0.5}$ = 96°C--.

Column 5, line 10, "aicd" should be --acid--.

Column 5, line 27, "propylene" should be --propenyl--.

Column 5, line 29 after "carboxylic" insert --acid--.

Signed and Sealed this

Eighteenth Day of November 1980

[SEAL]

Attest:

SIDNEY A. DIAMOND

Attesting Officer       Commissioner of Patents and Trademark